US00PP23101P2

(12) United States Plant Patent
Tristram

(10) Patent No.: US PP23,101 P2
(45) Date of Patent: Oct. 9, 2012

(54) ***ERYSIMUM* PLANT NAMED 'WALFRASTAR'**

(50) Latin Name: *Erysimum×hybrida*
Varietal Denomination: WALFRASTAR

(76) Inventor: David Tristram, Arundel (GB)

( * ) Notice: Subject to any disclaimer, the term of this patent is extended or adjusted under 35 U.S.C. 154(b) by 0 days.

(21) Appl. No.: 13/065,991

(22) Filed: Apr. 5, 2011

Related U.S. Application Data

(60) Provisional application No. 61/343,763, filed on May 4, 2010.

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell

(57) ABSTRACT

A new and distinct variety of *Erysimum* plant named 'WALFRASTAR' which is characterized by compact freely-branching habit, variegated foliage, bright yellow sweetly scented sterile flowers which are produced from spring until late summer. In combination these traits set 'WALFRASTAR' apart from all other existing varieties of *Erysimum* known to the inventor.

2 Drawing Sheets

Genus: *Erysimum.*
Species: ×*hybrida.*
Denomination: 'WALFRASTAR'.

BACKGROUND OF THE INVENTION

This application claims the benefit of priority under 35 U.S.C. 119(e) of U.S. Provisional Application No. 61/343,763 filed on May 4, 2010, entitled *Erysimum* PLANT NAMED 'WALFRASTAR'.

The present invention relates to a new and distinct cultivar of *Erysimum*, also commonly known as perennial wallflower, which is grown as an ornamental for use in planted containers and in the garden and landscape. The new cultivar is known botanically as *Erysimum×hybrida*, and will be referred to hereinafter by the cultivar name 'WALFRASTAR'.

'WALFRASTAR' arose and was discovered by the inventor in 2006 as a naturally occurring variegated branch sport on a single plant in a crop of the inventor's variety of *Erysimum* plant named 'WALFRASUN' (U.S. Plant Pat. No. 13,432). 'WALFRASUN' is non-variegated. The only other cultivar of variegated *Erysimum* known to the inventor is the variety in commerce known variously as *Erysimum linifolium* 'Variegatum' or simply *Erysimum variegatum*, whose flowers are purple in color. The flowers of 'WALFRASTAR' are yellow in color as are the flowers of the parent variety 'WALFRASUN'.

'WALFRASTAR' was first asexually propagated by the inventor in 2007 in Walberton, West Sussex, England. Asexual propagation was accomplished using softwood cuttings. Since that time, under careful observation, the distinguishing characteristics of 'WALFRASTAR' have been determined stable and uniform, and to reproduce true to type in successive generations of asexual propagation.

SUMMARY OF THE INVENTION

The distinguishing characteristics of 'WALFRASTAR' are as follows: In combination these traits set 'WALFRASTAR' apart from all other existing varieties of *Erysimum* known to the inventor. 'WALFRASTAR' has not been tested under all possible conditions and phenotypic differences may be observed with variations in environmental, climatic, and cultural conditions.

1. 'WALFRASTAR' is hardy and perennial in USDA Zone 7 and warmer.
2. The growth habit of 'WALFRASTAR' is compact due to its short internodes and freely-branching structure.
3. The foliage of 'WALFRASTAR' is variegated, consisting of cream colored margins on gray-green leaves.
4. The flowers of 'WALFRASTAR' are bright yellow and sweetly scented.
5. The flowers of 'WALFRASTAR' are sterile.
6. The flower buds of 'WALFRASTAR' are mauve and contrast strongly with the bright yellow flowers.
7. 'WALFRASTAR' blooms from spring until late summer.
8. 'WALFRASTAR' achieves a height of 30 cm and a spread of 20 cm in the first year of growth.
9. 'WALFRASTAR' achieves a height of 30 cm-40 cm and a spread of 30 cm-40 cm when mature and established as a perennial.
10. 'WALFRASTAR' grows well in full sun to part shade, in fertile well-drained soil.
11. 'WALFRASTAR' is drought tolerant once established.

BRIEF DESCRIPTION OF THE DRAWINGS

The accompanying color drawings illustrate the overall appearance of 'WALFRASTAR' showing the colors of its foliage and flowers as true as it is reasonably possible to obtain in colored reproductions of this type. Both drawings have been made from a one year old plant which has been grown in a 1 liter container out of doors in Walberton, West Sussex, England.

The drawing labeled as FIG. 1 depicts a whole plant of 'WALFRASTAR' at time of first flowering, in the spring.

Figure 1:
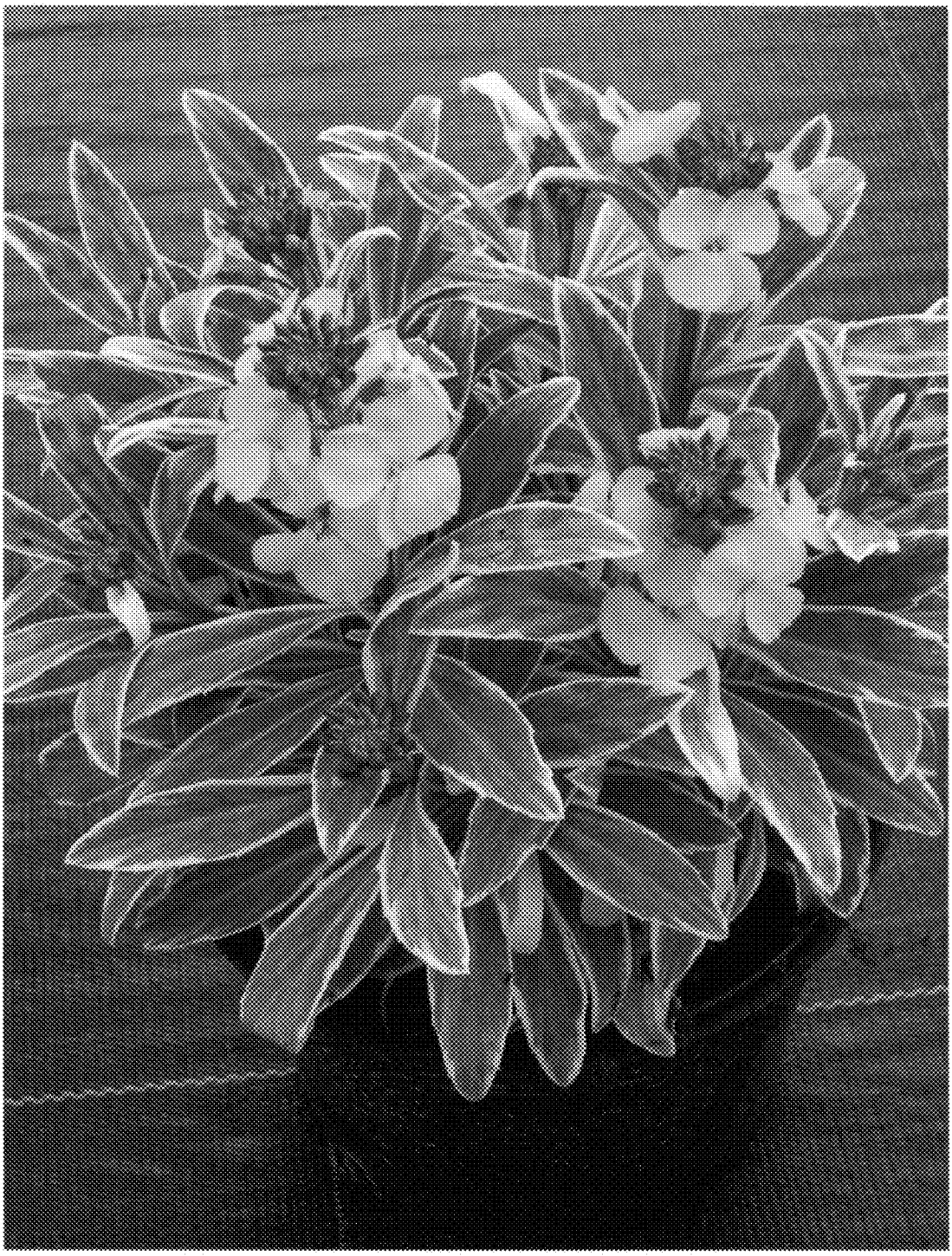
Figure 2:
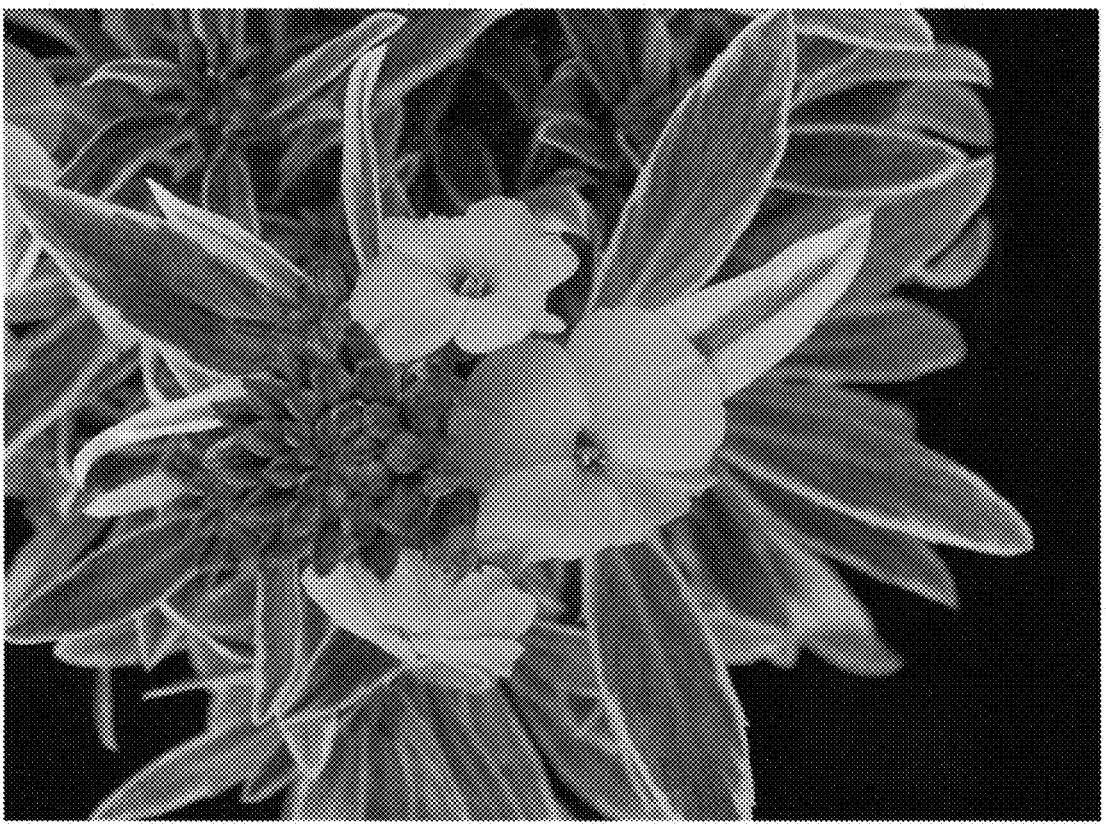

The drawing labeled as FIG. 2 depicts a close-up view of the inflorescence of 'WALFRASTAR' and depicts the bright yellow flowers and mauve-colored buds.

BOTANICAL DESCRIPTION OF THE PLANT

The following is a detailed description of 'WALFRASTAR' as grown in one-gallon containers out-of-doors in Sussex, England. The color determinations are in accordance with the fifth edition of The Colour Chart of The Royal Horticultural Society, London, England, except where general color terms of ordinary dictionary significance are used. Growing conditions, diseases and pests are similar to that of other *Erysimum*.

Botanical classification: Genus: *Erysimum*. Species: ×*hybrida*, or, as is common, that no species is ascribed to cultivars of *Erysimum*.

Cultivar: 'WALFRASTAR'.

Commercial classification: Perennial.

Common name: Wallflower.

Use: Ornamental for container or landscape.

Cultural requirements: Plant in full sun or partial shade and any free-draining soil.

Parentage: 'WALFRASTAR' resulted as a naturally occurring variegated branch mutation on a single plant in a crop of *Erysimum* 'WALFRASUN'.

Plant description:

*Bloom period*.—Main period of bloom is from April to July. Some blooming continues until October.

*Plant habit*.—Compact and freely branching.

*Vigor*.—Moderately vigorous, but less vigorous than the parent 'WALFRASUN'.

*Height*.—30 cm.

*Width*.—20 cm.

*Hardiness*.—USDA Zones 7-10.

*Root system*.—Fine.

*Propagation*.—Propagation is accomplished using softwood cuttings at 20° Celsius base temperature.

*Time to develop roots*.—Roots are produced within 3 weeks.

*Crop time*.—Eight months are required to produce a finished one-gallon container from a rooted cutting.

Stem:

*Shape*.—Round.

*Stem color*.—189B.

*Average stem dimensions*.—25 cm. in length and 0.50 cm. in diameter.

*Stem surface*.—Pubescent.

*Branching*.—Basal branching.

*Basal branch dimensions*.—2.50 cm. in diameter and 12-17 cm. in length.

*Basal branch surface*.—Furfuraceous.

*Basal branch color*.—197A.

*Internode distance*.—Ranges from 0.3 cm to 1.5 cm.

Foliage:

*Type*.—Evergreen.

*Shape*.—Lanceolate.

*Division*.—Simple.

*Apex*.—Acute.

*Base*.—Attenuate.

*Venation*.—Pinnate with central vein depressed on upper surface and protruding on lower surface.

*Vein color* (*upper and lower surfaces*).—189B.

*Margins*.—Entire with occasional small teeth.

*Arrangement*.—Alternate and spirally up stem.

*Attachment*.—Sessile.

*Surfaces* (*adaxial and abaxial*).—Slightly pubescent.

*Leaf dimensions*.—5-10 cm. in length and 8-15 mm. in width.

*Leaf color* (*both surfaces*).—189A with 190B in parts and edges of 18B.

*Fragrance*.—Absent.

Flowers:

*Type*.—Inflorescence.

*Shape*.—A combination of cruciform and explanate.

*Flower dimensions*.—17-24 mm. in width and 10-12 mm. in height.

*Persistent or self-cleaning*.—Self-cleaning.

*Aspect*.—Erect and facing upward.

*Quantity*.—Numerous. Approximately 10 inflorescences are evident (in bud and in flower) at any one time in the summer months. By fall, approximately 100-120 inflorescences have been formed.

*Inflorescence dimensions* (*at maturity*).—15-25 cm. in length and 2-3 mm. in diameter with 4-5 flowers per cm. and spaced 4 cm. from the end of the inflorescence.

*Type of inflorescence*.—Bractless racemes.

*Throat depth*.—6-9 mm.

*Lastingness*.—7-10 days on the plant.

*Fragrance*.—Strong, sweet scent.

*Sexuality*.—Bisexual.

*Bud dimensions*.—3-4 mm. in width and 6-9 mm. in length.

*Bud shape*.—Ovate and slightly flattened.

*Bud color*.—Closest to 166A.

*Flower color*.—14A.

*Petals*.—Four in number.

*Fused or unfused*.—Unfused.

*Petal dimensions*.—8 mm. in length and 8 mm. in width with further 8 mm.×1 mm. inside the calyx.

*Petal shape*.—Orbicular.

*Petal apex*.—Rounded.

*Petal base*.—Attenuate.

*Petal color* (*both surfaces*).—14A.

*Petal margin*.—Entire.

*Petal surface*.—Glabrous.

*Calyx dimensions*.—3-4 mm. in diameter, 10 mm. in length.

*Calyx color*.—166A.

*Calyx surface*.—Pubescent.

*Sepals*.—Four in number.

*Sepals fused or unfused*.—Unfused.

*Sepal margin*.—Entire.

*Sepal shape*.—Lanceolate.

*Sepal apex*.—Acute.

*Sepal color* (*both surfaces*): 144D except brown at apex (ranges between 172A and 176A) and pink 181D towards base.

*Sepal dimensions*.—9 mm. in length and 2 mm. in width.

*Peduncle dimensions*.—4-6 mm. in length and 1 mm. in diameter.

*Peduncle color*.—198A.

*Peduncle surface*.—Pubescent.

*Pedicel dimensions*.—6 mm. in length, 1 mm. in diameter.

*Pedicel color*.—139D.

Reproductive organs:

*Stamens*.—Six in number.

*Stamen color*.—8C.

*Stamen dimensions*.—5-8 mm. in length and 0.5-1.0 mm. in diameter.

*Anther color*.—11B.

*Anther shape*.—Linear.

*Anther dimensions*.—0.5 mm. in width and 2 mm. in length.

*Pollen color*.—11B.

*Amount of pollen*.—Small amount.
*Pistil*.—One.
*Pistil length*.—2 mm. in length.
*Pistil shape*.—Club-shaped.
*Pistil color*.—151C.
*Stigma shape*.—Bifid.
*Stigma color*.—151C.
*Stigma dimensions* (*both lobes together*).—length 1.5 mm, width 0.75 mm, depth 2 mm.
*Style color*.—151B.
*Style length*.—2 mm. in length.
*Ovary position*.—Superior.
*Ovary color*.—191C.
*Ovary shape*.—Long, narrow and cylindrical.
*Ovary dimensions*.—5 mm. in height and 1.5 mm. in diameter.

Seed production: None, after repeated observation. Variety is sterile.

The invention claimed is:

1. A new and distinct variety of *Erysimum* plant named 'WALFRASTAR' as described and illustrated.

* * * * *